(12) United States Patent
Juneau et al.

(10) Patent No.: US 6,761,789 B2
(45) Date of Patent: Jul. 13, 2004

(54) METHOD OF MANUFACTURING A SOFT HEARING AID

(75) Inventors: Roger P. Juneau, Destrehan, LA (US); Lynn P. Creel, Kenner, LA (US); Edward J. Desporte, Covington, LA (US); Michael Major, Kenner, LA (US); Gregory R. Siegle, Kenner, LA (US); Kelly M. Kinler, Luling, LA (US)

(73) Assignee: Softear Technologies, L.L.C., Harahan, LA (US)

( * ) Notice: Subject to any disclaimer, the term of this patent is extended or adjusted under 35 U.S.C. 154(b) by 143 days.

(21) Appl. No.: 10/097,540

(22) Filed: Mar. 11, 2002

(65) Prior Publication Data

US 2002/0198437 A1 Dec. 26, 2002

Related U.S. Application Data

(60) Division of application No. 09/311,156, filed on May 13, 1999, now Pat. No. 6,354,990, which is a continuation-in-part of application No. 09/181,539, filed on Oct. 28, 1998, and a continuation-in-part of application No. 09/181,540, filed on Oct. 28, 1998, now Pat. No. 6,432,247, and a continuation-in-part of application No. 09/181,541, filed on Oct. 28, 1998, now Pat. No. 6,438,244, and a continuation-in-part of application No. 08/181,842, filed on Oct. 28, 1998, now Pat. No. 6,254,526, and a continuation-in-part of application No. 09/181,843, filed on Oct. 28, 1998, now Pat. No. 6,434,248, and a continuation-in-part of application No. 09/181,844, filed on Oct. 28, 1998, now Pat. No. 6,228,020, and a continuation-in-part of application No. 09/181,845, filed on Oct. 28, 1998, now Pat. No. 6,473,512, which is a continuation-in-part of application No. 09/084,864, filed on May 26, 1998, now Pat. No. 6,022,311.

(60) Provisional application No. 60/068,036, filed on Dec. 18, 1997.

(51) Int. Cl.⁷ ............... B29C 33/40; B29C 33/42

(52) U.S. Cl. .............. 156/245; 156/329; 156/344; 264/134; 264/135; 264/222; 264/225; 264/226; 264/227; 264/272.11; 264/272.14; 264/272.15; 427/301

(58) Field of Search ............. 156/245, 329, 156/344; 264/134, 135, 222, 225–227, 272.11, 272.14, 272.15; 427/301

(56) References Cited

U.S. PATENT DOCUMENTS 3,527,901 A * 9/1970 Geib ............... 381/328
RE33,017 E * 8/1989 Bellafiore ........... 381/68.6
4,871,502 A * 10/1989 LeBisch et al. ....... 264/222

* cited by examiner

*Primary Examiner*—Suzanne E. McDowell
(74) *Attorney, Agent, or Firm*—Garvey, Smith, Nehrbass & Doody, L.L.C.; Seth M. Nehrbass; Charles C. Garvey, Jr.

(57) ABSTRACT

A hearing aid instrument of the in-the-ear type (and preferably CIC) provides a receptacle with electronic hearing aid components mounted thereto. The receptacle has a cavity for holding electronic components (eg. battery, microphone, amplifier). A soft polymeric body is preliminarily formed by encapsulating a plurality of the electronic hearing aid component shaped inserts. The body is soft and is shaped to conform to the ear canal of the user. After forming, the insert is removed to provide an insert cavity that can carry electronic components. The soft polymeric body and encapsulated electronic hearing aid components define a soft structure compliant to the ear canal during use and that is substantially solid and free of void spaces between at least some of the components and the ear canal. This combination of soft compliant structure and encapsulated electronic hearing aid components addresses problems of peripheral leakage, poor fit, pivotal displacement that occurs with jaw motion and internal cross talk of components housed in prior art hollow type hearing aids.

25 Claims, 10 Drawing Sheets

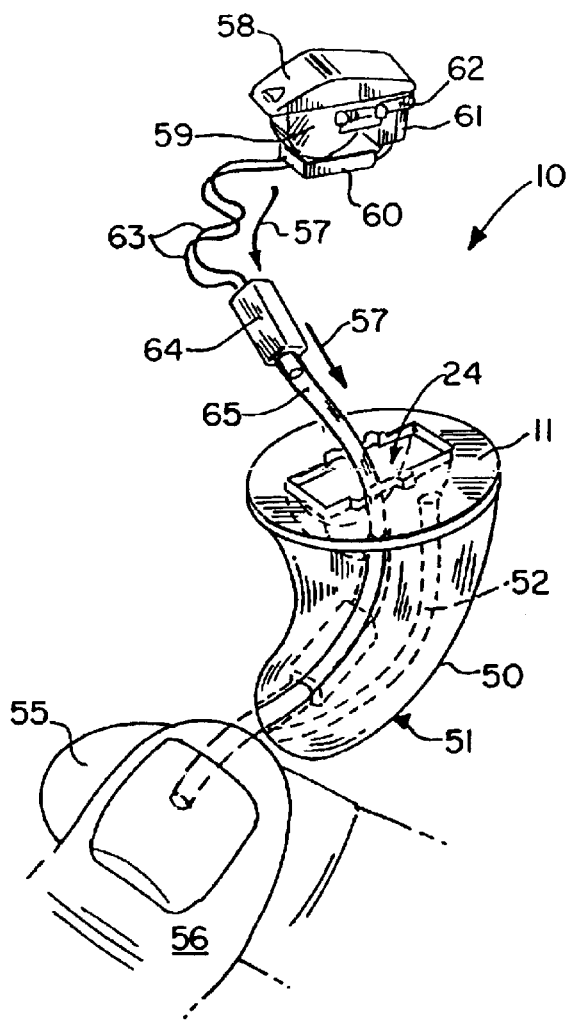
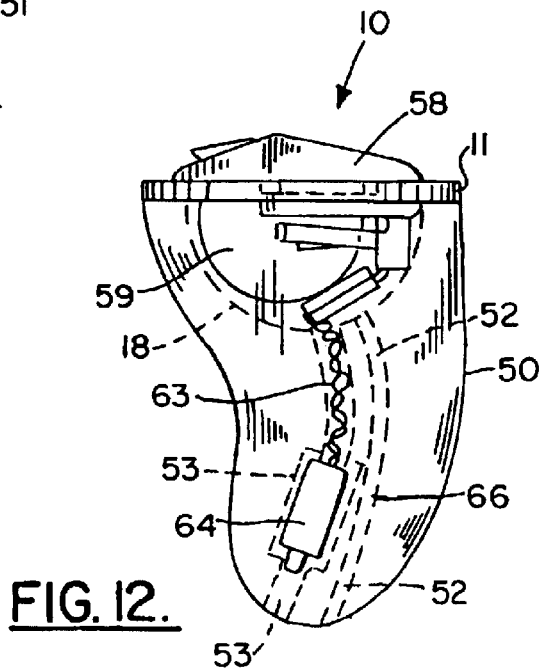
FIG. 11.
FIG. 12.

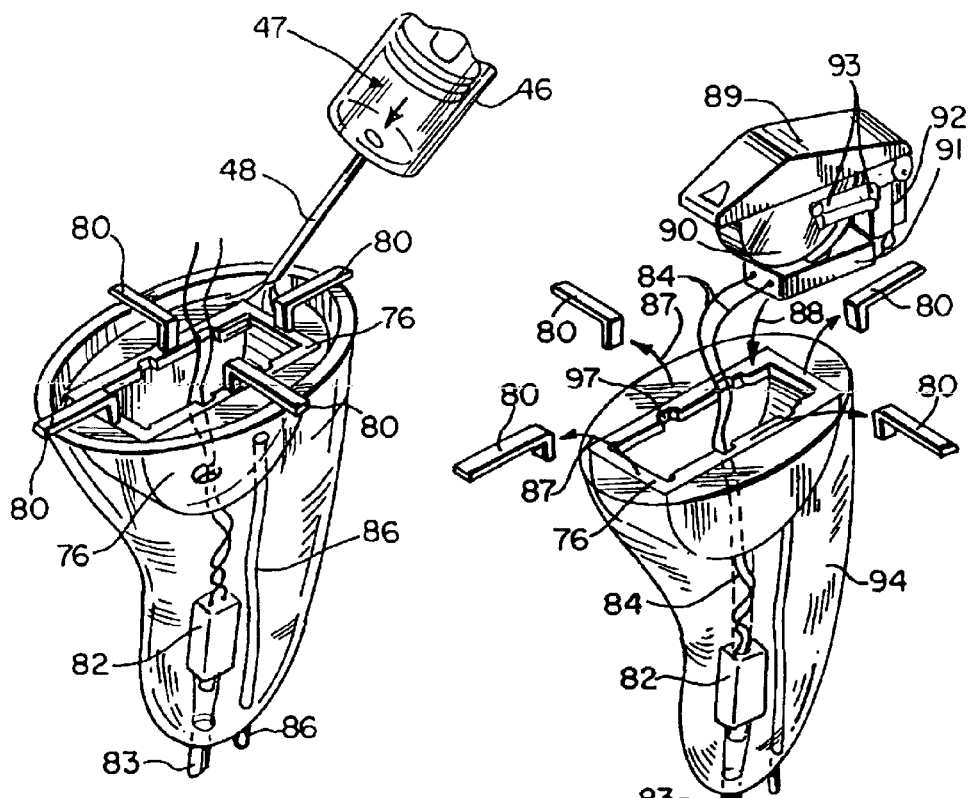
FIG. 15.
FIG. 16.
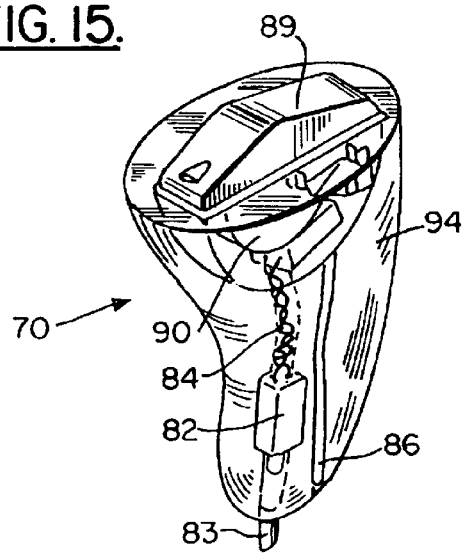
FIG. 17.

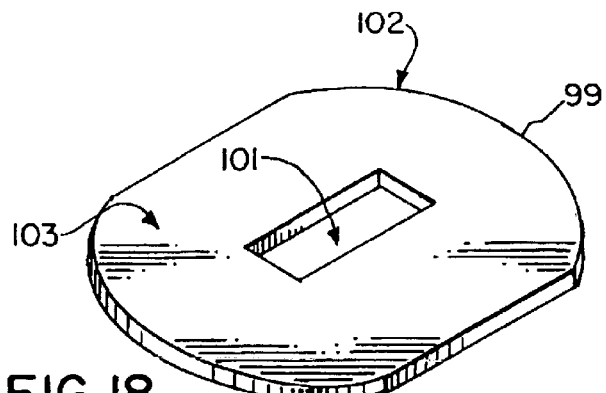
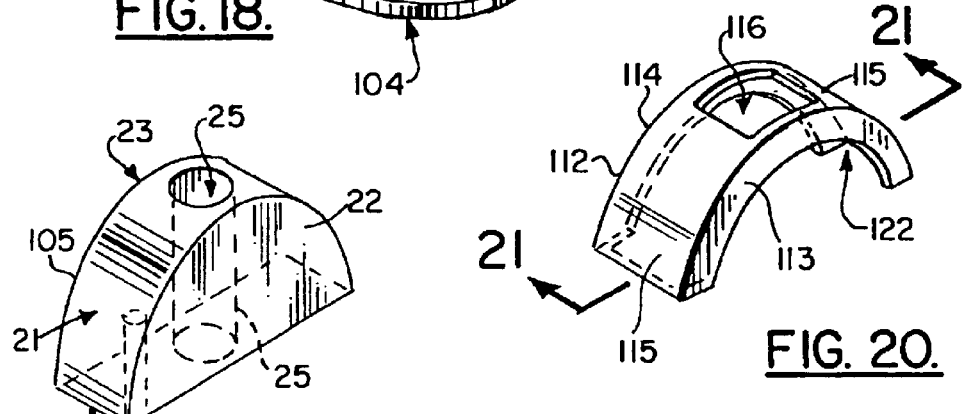
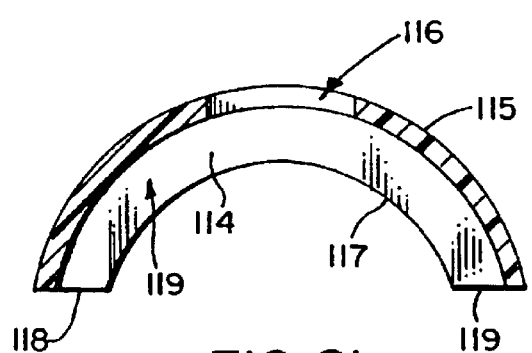

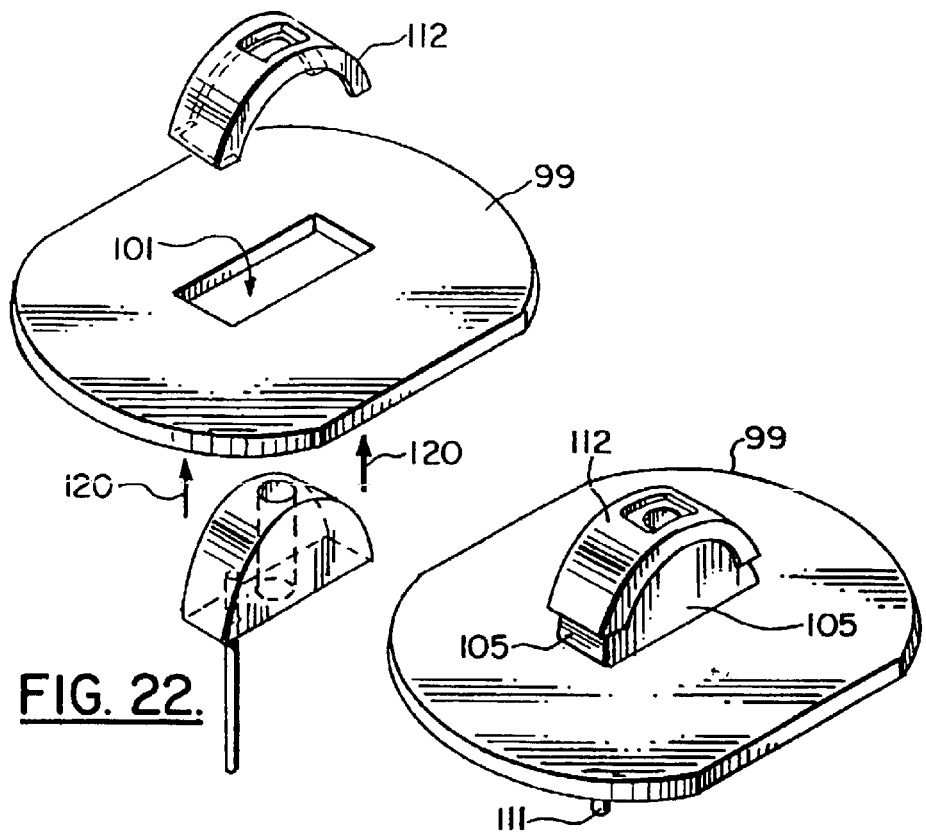
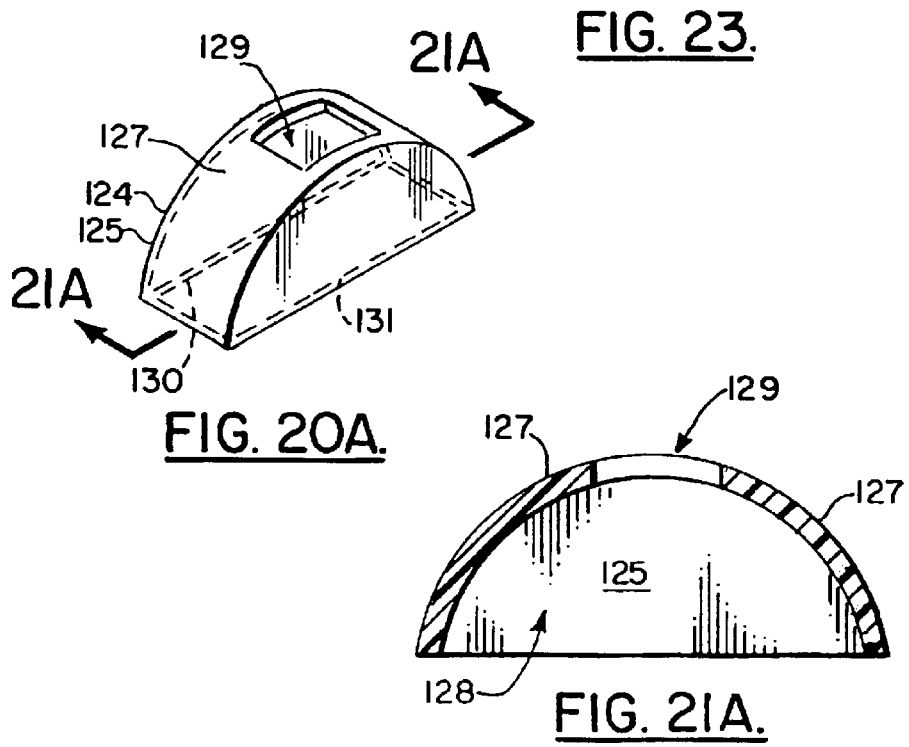
FIG. 22.
FIG. 23.
FIG. 20A.
FIG. 21A.

METHOD OF MANUFACTURING A SOFT HEARING AID

CROSS-REFERENCE TO RELATED APPLICATIONS

This application is a divisional of U.S. patent application Ser. No. 09/311,156, filed May 13, 1999, now U.S. Pat. No. 6,354,990; which is a continuation-in-part application of U.S. patent application Ser. Nos. 09/181,539; 09/181,540, now U.S. Pat. No. 6,432,247; Ser. No. 09/181,541, now U.S. Pat. No. 6,438,244; Ser. No. 09/181,842, now U.S. Pat. No. 6,254,526; Ser. No. 09/181,843, now U.S. Pat. No. 6,434,248; Ser. No. 09/181,844, now U.S. Pat. No. 6,228,020; and Ser. No. 09/181,845, now U.S. Pat. No. 6,473,512; all filed Oct. 28, 1998, which are continuations-in-part of application Ser. No. 09/084,864, now U.S. Pat. No. 6,022,311, filed May 26, 1998, which claims benefit of U.S. Patent Application Serial No. 60/068,036, filed Dec. 18, 1997; all incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to hearing aids and more particularly to an improved hearing aid, its method of manufacture and an improved method of compensating for hearing loss. More particularly, the present invention provides an improved method and apparatus for compensating for hearing loss that uses a construction combining a mounting receptacle (for example, a receptacle or modular face plate or semi-modular face plate) with a soft polymeric body that is joined to the mounting member and which encapsulates some of the electronic hearing aid components of the apparatus, the soft polymeric body being sized and shaped to conform to the user's ear canal during use. It may be possible to use a soft polymeric material as the receptacle or face plate.

2. General Background of the Invention

The hearing industry has realized major strides in the development of high-fidelity, high-performance products, the most recent of which is digital signal processing technology. Hearing care professionals expected those advancements to solve the shortcomings of traditional amplification, and to push the market forward. Those expectations have not been fully realized. While these developments have solved many of the problems associated with traditional electronic design and steadily gained market share, they have not fostered overall market growth.

The issues of early acoustic feedback, less than optimum fidelity and intermodulation of the frequency response cannot be completely resolved by electronic manipulation of the signal by either analog or digital means.

Historically, custom-molded ear worn hearing instruments have been limited to an "acrylic pour" process as the means of the construction. With the advent of miniaturization and technological advancement of computer chip programming, the ear-worn instruments have become smaller and are positioned into the bony portion of the ear canal, commonly referred to as "deep insertion technology".

Developments outside the hearing industry have culminated in a new level of micro-miniaturization of electronic components for industry applications. Consequently, advanced signal processing can be housed in less space than was required for traditional electro-acoustic components.

With the development of programmable hearing aids, using either analog or digital signal processing, custom electronic design has shifted from the manufacturing level to the clinical level. The clinician can now customize the electro-acoustic response via software. It is no longer necessary for the device to be returned to the manufacturer for hardware changes to arrive at the desired electro-acoustic response. However, it is still often necessary to return the device for shell modifications.

In direct contrast to electronic advances within the industry, little or no advancement has been realized in custom prosthetic design. Since the late 1960's, when the custom in-the-ear hearing aid was developed, materials and construction techniques remained virtually unchanged. These materials and techniques were adopted from the dental industry, whereby the customized housing-commonly called a "shell" was constructed using acrylic of 90 point Durometer Hardness Shore D. This construction process provided the structure and the strength of material necessary to protect the electronics.

At the time the acrylic shell was developed, hearing instruments were worn in the relatively forgiving cartilaginous portion of the ear canal. Micro-miniaturization of electronic components, combined with increased consumer demand for a cosmetically acceptable device, has shifted the placement of the hearing aid toward the bony portion of the ear canal.

The bony portion of the canal is extremely sensitive and intolerant of an acrylic shell when that shell is over sized due to standard waxing procedures or is in contact with the canal wall beyond the second anatomical bend. Rigid acrylic that does not compress must pivot in reaction to jaw or head movement, thereby changing the direction of the receiver yielding a distorted acoustic response. In addition, the pivot action causes displacement of the device resulting in unwanted acoustic feedback. This problem has necessitated countless shell modifications, thereby compromising the precision approach of the original dental technology. Many such devices require some modification by the manufacturer. Most manufacturers can expect a high percentage of returns for modification or repair within the first year. Consequently, CIC (completely in canal) shell design has been reduced to more of a craft than a science. Although the recent introduction of the ultra-violet curing process has produced a stronger, thinner shell, the overall Shore Hardness remained unchanged.

The current trend for custom hearing aid placement is to position the instrument toward the bony portion of the ear canal. The ear canal can be defined as the area extending from the concha to the tympanic membrane. It is important to note that the structure of this canal consists of elastic cartilage laterally, and porous bone medially. The cartilaginous portion constitutes the outer one third of the ear canal. The medial two-thirds of the ear canal is osseous or bony. The skin of the osseous canal, measuring only about 0.2 mm in thickness, is much thinner than that of the cartilaginous canal, which is 0.5 to 1 mm in thickness. The difference in thickness directly corresponds to the presence of apocrine (ceruminous) and sebaceous glands found only in the fibro-cartilaginous area of the canal. Thus, this thin-skinned thinly-lined area of the bony canal is extremely sensitive to any hard foreign body, such as an acrylic hearing instrument.

Exacerbating the issue of placement of a hard foreign body into the osseous area of the ear canal is the ear canal's dynamic nature. It is geometrically altered by temporomandibular joint action and by changes in head position. This causes elliptical elongation (widening) of the ear canal. These alterations in canal shape vary widely from person to person. Canal motion makes it very difficult to achieve a comfortable, true acoustic seal with hard acrylic material. When the instrument is displaced by mandibular motion, a leakage or "slit leak" creates an open loop between the receiver and the microphone and relates directly to an electro-acoustic distortion commonly known as feedback. Peripheral acoustic leakage is a complex resonator made up of many transient resonant cavities. These cavities are transient because they change with jaw motion as a function of time, resulting in impedance changes in the ear canal. These transients compromise the electro-acoustic performance.

The properties of hard acrylic have limitations that require modification to the hard shell exterior to accommodate anatomical variants and the dynamic nature of the ear canal. The shell must be buffed and polished until comfort is acceptable. The peripheral acoustic leakage caused by these modifications results in acoustic feedback before sufficient amplification can be attained.

Hollow shells used in today's hearing aid designs create internal or mechanical feedback pathways unique to each device. The resulting feedback requires electronic modifications to "tweak" the product to a compromised performance or a "pseudo-perfection". With the industry's efforts to facilitate the fine-tuning of hearing instruments for desired acoustic performance, programmable devices were developed. The intent was to reduce the degree of compromise, but by their improved frequency spectrum the incidence of feedback was heightened. As a result, the industry still falls well short of an audiological optimum.

A few manufacturers have attempted all-soft, hollow shells as alternatives to acrylic, hollow shells. Unfortunately, soft vinyl materials shrink, discolor, and harden after a relatively short period of wear. Polyurethane has proven to provide a better acoustic seal than polyvinyl, but has an even shorter wear life (approximately three months). Silicones have a long wear life but are difficult to bond with plastics such as acrylic, a necessary process for the construction of custom hearing instruments. To date, acrylic has proven to be the only material with long term structural integrity. The fact remains, however, that the entire ear is a dynamic acoustic environment and is ill-served by a rigid material such as acrylic. Also, the acrylic hearing aids typically need to be returned to the manufacturer for major shell modifications.

The following references are all incorporated herein by reference:

U.S. Pat. Nos.: 4,051,330; 4,375,016; 4,607,720; 4,716,985; 4,811,402; 4,870,688; 4,880,076; 4,937,876; 5,002,151; 5,068,902; 5,185,802; 5,201,007; 5,259,032; 5,530,763; 5,430,801; 5,500,902; and 5,659,621.

Also of interest and incorporated herein by reference are published Japanese patent application no. JA61-238198, the articles from December 1997 Journal of American Academy of Audiology, and Staab, Wayne J. and Barry Finlay, "A fitting rationale for deep fitting canal hearing instruments", Hearing Instruments, Vol. 42, No. 1, 1991, pp. 7–10, 48.

BRIEF SUMMARY OF THE INVENTION

The present invention provides a method of constructing a hearing aid and a soft hearing instrument that is solid (i.e. eliminates void spaces). This instrument includes a soft body portion that is truly soft, comprising an elastomer of about 3 to 55 Durometer Shore A and preferably 10–35 Durometer Shore A. This product is unique in that it is solid, with the electronic components actually encapsulated or embedded within the soft fill material. The fill material can be a Dow Corning® MDX-4-4210 silicone or a silicone polymer distributed by Factor II, Inc. of Lakeside, Ariz., designated as product name 588A, 588B, 588V.

The present invention provides a method that can replace traditional acrylic shell construction. Unlike the shell construction process, the ear impression is not modified, built up, or waxed. With the elimination of these steps, a more faithful reproduction of the ear impression is accomplished. With the present invention, the manufacturer should be able to produce a hearing aid body which will not need to be returned as frequently for modification as with present hard acrylic hearing aid bodies.

The apparatus of the present invention is virtually impervious to the discoloration, cracking, and hardening experienced with polyvinyls and polyurethanes.

The hearing aid of the present invention provides a greater range of gain before feedback occurs.

The outer surface of the body of the present invention is preferably non-absorbent and virtually impervious to cerumen.

As used herein, "in-the-ear hearing aids" includes all hearing aids which have all of the electronics positioned in the ear, and thus includes hearing aid styles ranging from full concha to CIC (completely in the canal) hearing aid styles.

The preferred embodiment of the present invention shown in the drawings is a CIC hearing aid style.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIGS. 11 and 12 are perspective views illustrating the final method steps of the method of the present invention including the assembly of electronic components to the soft elastomer body;

FIGS. 15–17 are perspective, schematic views illustrating the method of the present invention;

FIG. 17 is a perspective view of the preferred embodiment of the apparatus of the present invention;

FIG. 18 is a fragmentary perspective view of a third embodiment of the apparatus of the present invention showing the mounting plate portion of the mounting member;

FIG. 19 is a perspective, fragmentary view of the third embodiment of the apparatus of the present invention illustrating one of the insert portion thereof;

FIGS. 20–20A are fragmentary perspective views of the third embodiment of the apparatus of the present invention showing the receptacle portion of the mounting member;

FIGS. 21–21A are partial, sectional, fragmentary views of the receptacle of FIG. 20;

FIG. 22 is a fragmentary, perspective view of the third embodiment of the apparatus of the present invention illustrative the mounting member including mounting plate and receptacle portions thereof and the insert portion thereof;

FIG. 23 is a fragmentary, perspective view of the third embodiment of the apparatus of the present invention illustrating the mounting member and insert portions thereof;

DETAILED DESCRIPTION OF THE INVENTION

Figure 1:
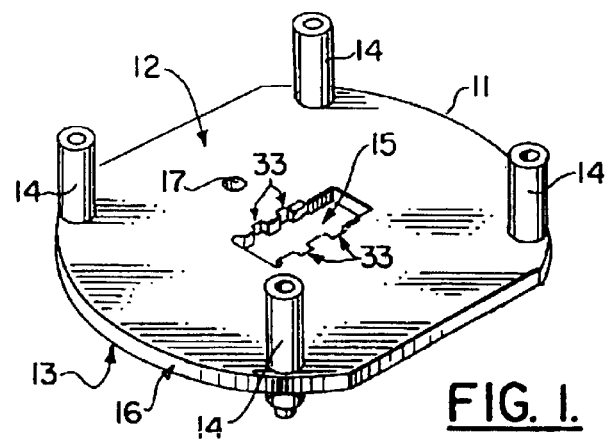
FIG. 1 is a fragmentary, perspective view of the preferred embodiment of the apparatus of the present invention showing the mounting member portion thereof.

In FIGS. 1–12, there can be seen a method for constructing a hearing aid apparatus that is culminated in the addition of electronic components to the hearing aid apparatus as shown in FIGS. 11 and 12. FIG. 12 shows the completed hearing aid apparatus designated generally by the numeral 10.

Hearing aid apparatus 10 is constructed with a beginning modular face plate 11 having a surface 12 and an opposing surface 13. A plurality of stacking pins 14 can be provided at the periphery 16 of modular face plate 11. Pins 14 enable shipments of several stacked modular face plates 11 with electronic components being placed therebetween.

A central opening 15 receives insert 19 during construction using the method of the present invention. The modular face plate 11 also becomes a part of the apparatus 10 of the present invention after construction is completed wherein the central opening 15 receives an electronic component carrying receptacle 18. Modular face plate 11 has an opening 17 that receives an end portion of a vent tube as will be described more fully hereinafter.

The combination of modular face plate 11 and insert 19 are used to form a soft elastomeric or polymeric (eg. silicone) body 50 that will carry electronic hearing aid components to define a hearing aid electronics package during use. The insert 19 is best seen in FIGS. 2–5. The insert 19 and face plate 11 are used to construct soft elastomeric or polymeric body 50 as shown in FIGS. 6–10.

In FIGS. 2–5, insert 19 includes an insert body 20 having a curved surface 21, a pair of opposed semi-circular flat surfaces 22, 23, and flat surface 24. Insert body 20 includes a cylindrical bore 25 that enables insert body 20 to be mounted on elongated, coated (eg. Teflon®) wire 27. Insert body 20 also provides an extraction handle 26 that aids in its removal from soft polymeric body 50 after molding is complete and the soft elastomeric body has set.

Figures 2, 3, 4, 5:
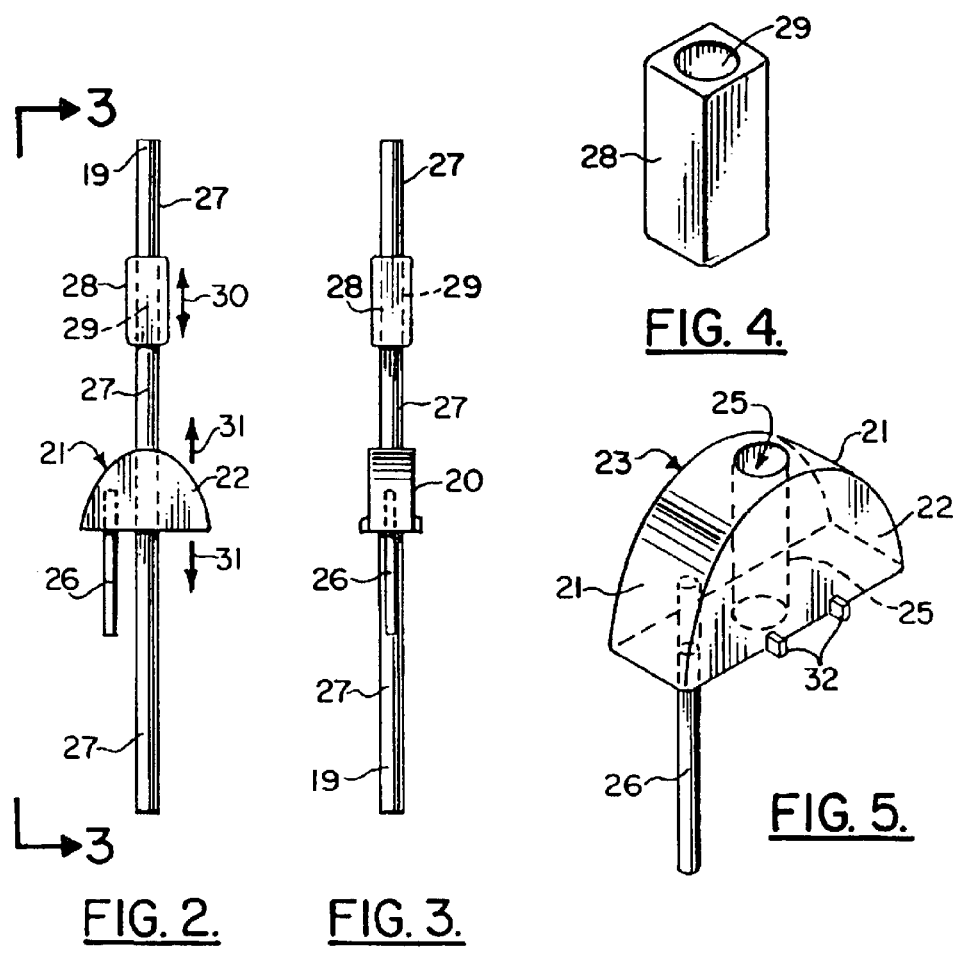
FIG. 2 is an elevational view of the insert portion of the preferred embodiment of the apparatus of the present invention.
FIG. 3 is an elevational side view of the insert portion of FIG. 2, taken along lines 3—3 of FIG. 2.
FIG. 4 is a fragmentary, perspective view of a portion of the insert in FIGS. 2 and 3.
FIG. 5 is a fragmentary, perspective view illustrating a portion of the insert of FIGS. 2 and 3.

In FIGS. 2–4, insert 19 also includes a receiver replica insert portion 28 having open ended bore 29. The open ended bore 29 enables the receiver replica insert 28 to be mounted on coated wire 27, as shown in FIGS. 2 and 3.

Each of the insert portions 20 and 28 can be adjustably, slidably mounted upon coated (eg. Teflon®) wire 27, as indicated schematically by the arrows 30, 31, in FIG. 2. This feature enables a desired spacing between insert 20 and insert 28 to be achieved prior to construction of the soft polymeric body 50. It should be understood that the insert members 20, 28 can be of different size and configuration. The insert 28 is typically a receiver replica insert that can be configured to duplicate the size and shape of any number of commercially available receivers or custom receivers. Similarly, the insert 20 is an insert that is of the size and shape of a receptacle 18 that will carry a number of electronic hearing aid components such as, for example, a battery, microphone, amplifier, etc.

Figure 6:
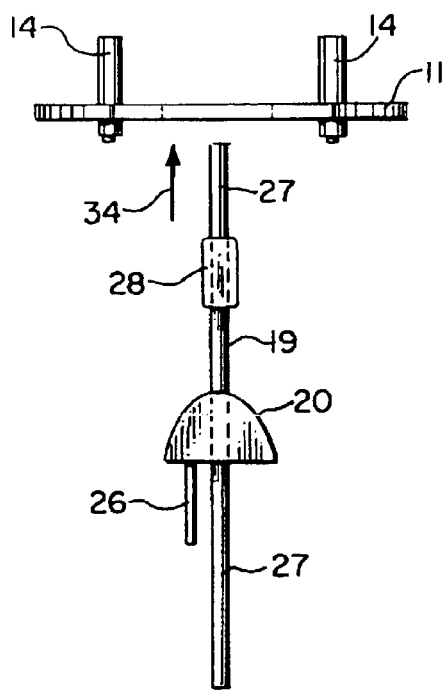
FIG. 6 is a fragmentary, elevational view of the preferred embodiment of the apparatus of the present invention illustrating the mounting member and insert portions thereof.

Insert body 20 can be provided with a plurality of tabs 32 that fit sockets 33 next to central opening 15 as shown in FIGS. 1 and 5. Tabs 32 enable the insert body 20 to form a snap fit with modular face plate 11 at sockets 33 prior to the formation of soft polymeric body 50 using injected liquid elastomer (eg. Silicon). FIGS. 4 and 6 illustrate the attachment of insert 19 to modular face plate 11.

Figure 7:
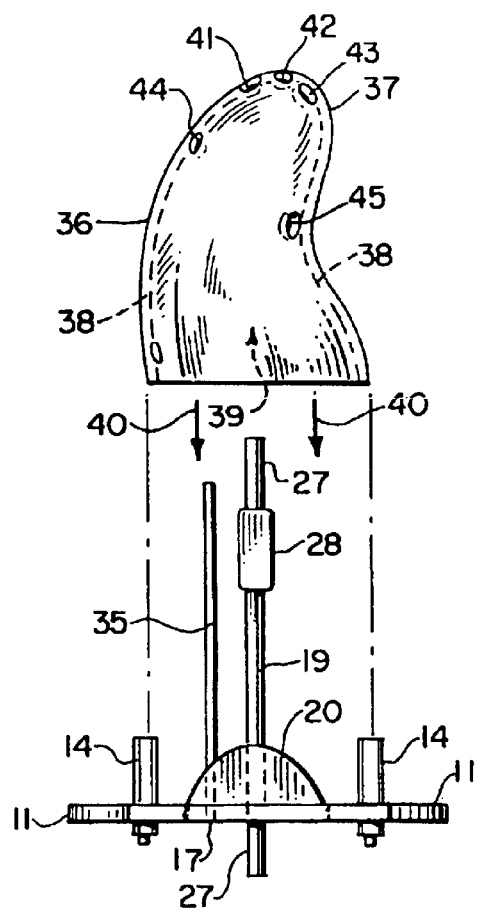
FIGS. 7 and 8 are schematic views illustrating the method of the present invention.
Figure 8:
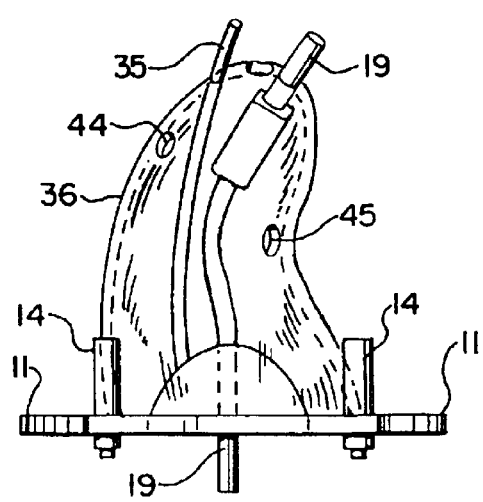

In FIG. 7, mold 36 is shown being attached to modular face plate 11 as indicated by arrows 40. In FIG. 7, vent tube replica insert 35 has been added to face plate 11 at opening 17. In FIG. 8, mold 36 has been attached to modular face plate 11 using a bonding material. The construction of mold 36 and its attachment to a mounting member such as modular face plate 11 is shown and described in more detail in prior co-pending patent application Ser. No. 09/181,540, filed Oct. 28, 1998, which is hereby incorporated herein by reference.

Figure 9:
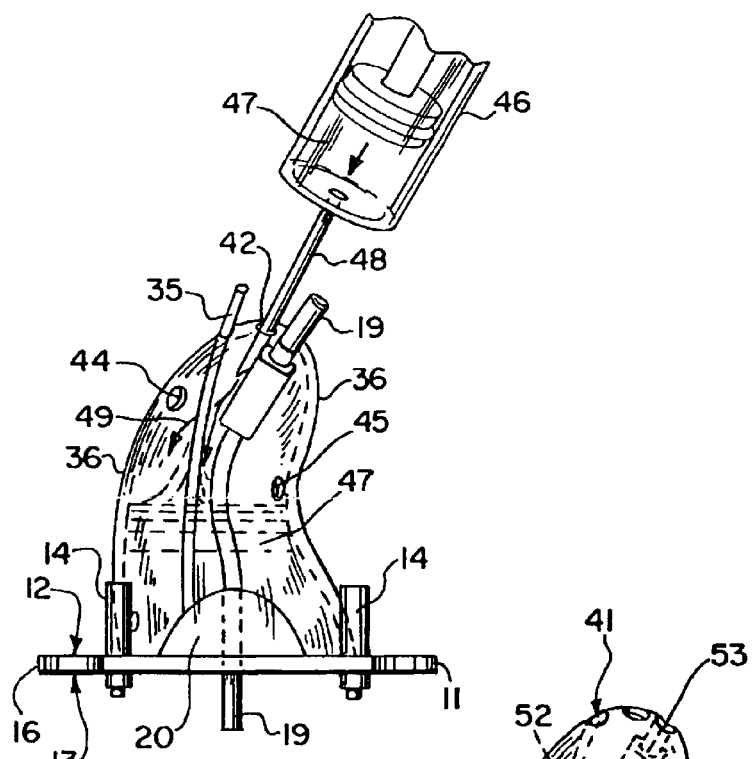
FIGS. 9 and 10 are additional schematic, perspective views illustrating the method of the present invention.
Figure 10:
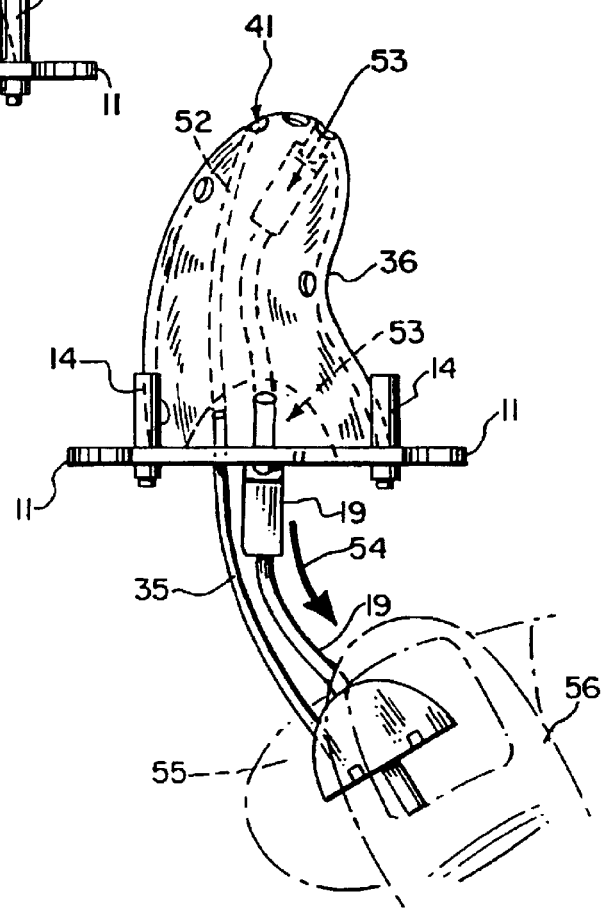

In FIGS. 7 and 8, mold 36 has an outer surface 37, a wall 38, and a cavity 39. A plurality of ports 41–45 are provided through the wall 38 as shown in FIGS. 7 and 8. In FIGS. 9 and 10, syringe 46 is shown adding elastomeric liquid material 47 through needle 48 into cavity 39, as indicated by arrow 49 in FIG. 9. The addition of elastomer 47 to cavity 39 encapsulates insert 19 and vent tube replica insert 35.

After the elastomer 47 is allowed to set, the insert 19 and vent tube replica insert 35 can be removed as indicated in FIG. 10. The insert 19 and vent tube replica insert 35 are shown gripped by a technician's finger 55 and thumb 56 and removed as indicated by arrow 54 from soft polymeric body 50 and mold 36. By removing the inserts 19, 35, a vent tube cavity 52 and an electronics cavity 53 are provided in soft polymeric body 50. An electronics package of a number of electronic components can then be added to cavities 52, 53.

In FIGS. 11 and 12, additional method steps of the present invention are shown. In FIG. 11, the soft polymeric body 50 is shown having an outer surface 51 after removal of mold 36 and after a trimming of modular face plate 11. The modular face plate 11 is trimmed so that it exactly fits the outside contour of outer surface 51 of soft polymeric body 50 as shown in FIGS. 11 and 12.

In FIG. 11, the cavities 52, 53 that remain after removal of the inserts 19, 35 are replaced with electronic hearing aid components that enable the hearing aid 10 to function, including the components that are added into the cavities 52, 53 as indicated by arrows 57 in FIG. 11. The electronic components that occupy cavities 52, 53 include eg. battery 59, battery door 58, amplifier 60, microphone 61, wire harness 63, receiver 64, receiver sound tube 65, and locking tabs 62 that interlock with sockets 33 of modular face plate 11.

The completed hearing aid apparatus 10 as shown in FIG. 12 with all of the electronic components in position, occupying the two cavities 52, 53. A vent tube 66 is a tube that extends the full length of soft polymeric body 50, forming a connection with opening 17 in modular face plate 11.

Figure 13:
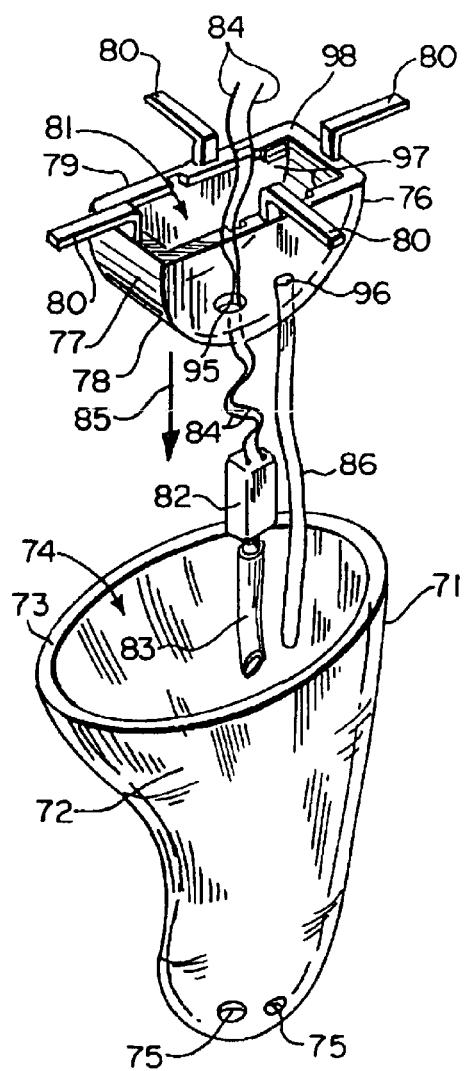
FIG. 13 is a perspective, exploded view of a second embodiment of the apparatus of the present invention.
Figure 14:
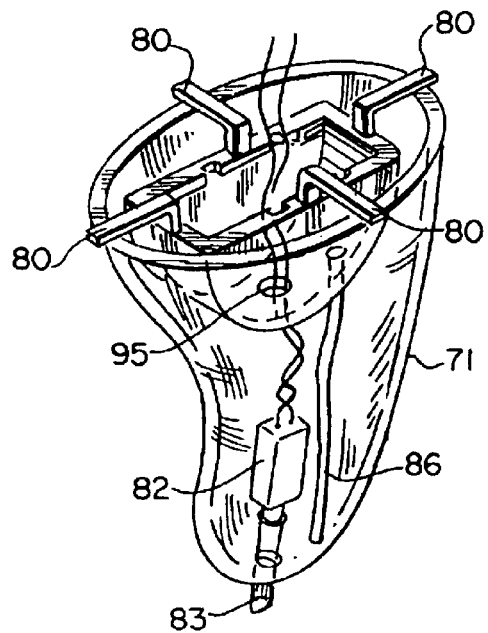
FIG. 14 is a perspective view of the second embodiment of the apparatus of the present invention shown prior to the addition of liquid polymeric or elastomeric material to the cavity.

In FIGS. 13–17, a second embodiment of the apparatus of the present invention is shown, designated generally by the numeral 70. Hearing aid apparatus 70 is constructed using an alternate method. In FIGS. 13 and 14, the hearing aid apparatus 70 begins with mold 71 having an outer surface 72, a wall 73 and a cavity 74. A number of ports 75 are formed through wall 73. A receptacle 76 that will carry electronic hearing aid components is attached to the mold wall 73 using a plurality of radially extending struts 80 as shown in FIGS. 13 and 14.

The receptacle 76 includes a pair of flat walls 78, 79 and a curved wall 77. This construction provides a cavity 81 for holding a number of electronic hearing aid components. Opening 95 in receptacle 76 enables a wiring harness 84 to pass through cavity 81 and into mold cavity 74 as shown in FIGS. 13 and 14. The components that extend through opening 95 and are external to cavity 81 of receptacle 76 include a portion of wiring harness 84, receiver 82, and receiver sound tube 83. Opening 96 in curved wall 77 of receptacle 76 enables vent tube 86 to pass through receptacle 76 curved wall 77 so that it can communicate with cavity 81.

The components that are contained with cavity 81 of receptacle 76 include battery 90, battery door 89, amplifier 91, microphone 92, and locking tabs 93 that form a connection with sockets 97 that are on the flat peripheral surface 98 of receptacle 76. In FIG. 13, the combination of the electronic components 82, 83, 84, 86, 89, 90, 91, 92 are attached to mold 71 in a temporary fashion using the radially extending struts as shown in FIGS. 13 and 14 and as indicated schematically by the arrow 85 in FIG. 13.

In FIG. 15, syringe 47 can be used to inject liquid polymeric or elastomeric material, such as silicone, through needle 48 into cavity 74 of mold 71. In this fashion, the cavity 74 is filled with soft polymeric or elastomeric material and encapsulates the electronic components that are below openings 95, 96. Additionally, the material injected through needle 48 surrounds receptacle 76, closely conforming to its curved wall 77 and flat walls 78, 79.

The interior cavity 81 of receptacle 76 is not filled with polymeric material so that the cavity 81 can be occupied by some of the electronic hearing aid components. This construction enables replacement of the electronic hearing aid components that are contained within the cavity 81 of receptacle 76 without intrusion into the soft polymeric body 94 that is formed when the elastomeric or polymeric material in 47 injected with syringe 46 is allowed to set.

In FIG. 16, the radially extending struts 80 have been removed as indicated by arrows 87. Arrow 88 indicates the addition of electronic hearing aid components to the cavity 81, namely battery 90, battery door 89, amplifier 91, microphone 92 and locking tabs 93. The completed hearing aid apparatus 70 is shown in FIG. 17.

Figure 28:
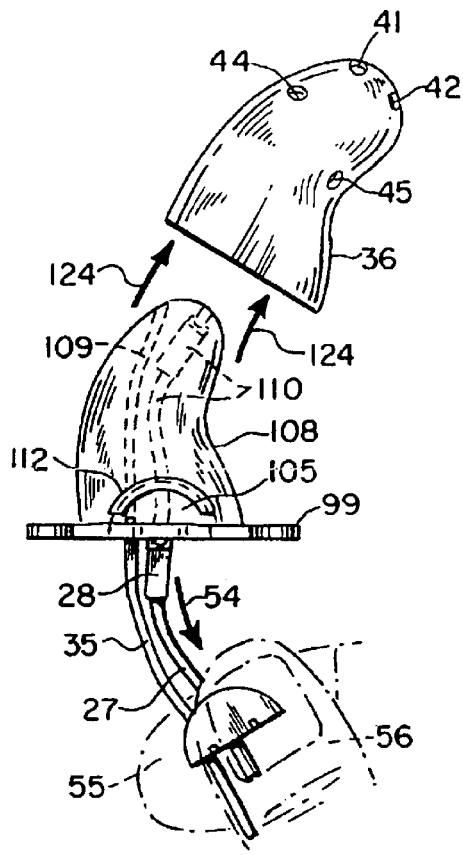
FIG. 28 is a perspective view of the third embodiment of the apparatus of the present invention illustrating the step of removing the shell from the soft polymeric bodies and the removal of the insert portions.
Figure 29:
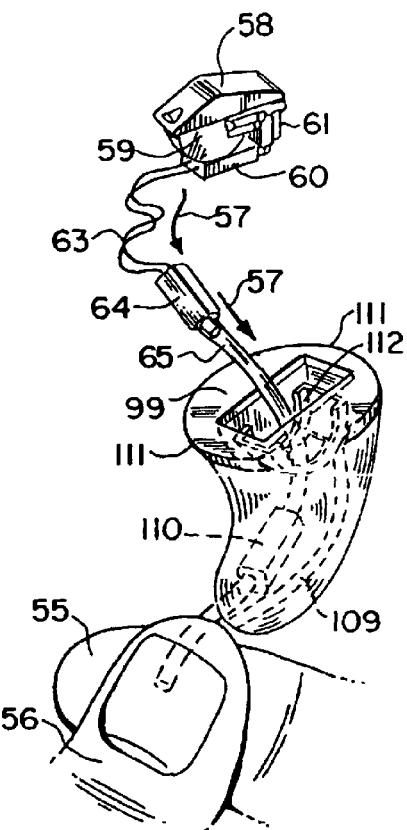
FIG. 29 is a perspective view of the method of constructing the third embodiment of the apparatus of the present invention showing the step of inserting the electronic hearing aid components into the soft polymeric body and mounting members.
Figure 30:
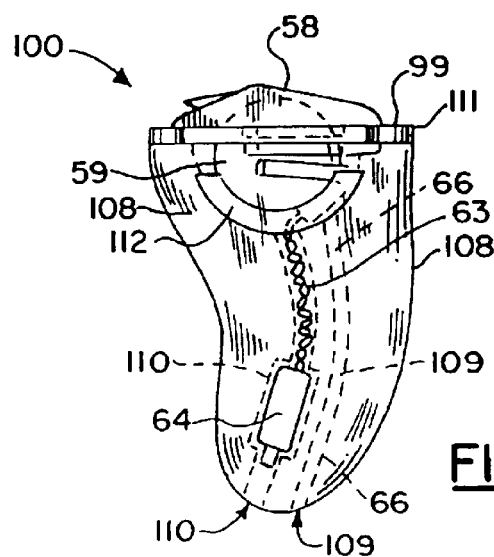
FIG. 30 is a perspective view of the third embodiment of the apparatus of the present invention.

FIGS. 18–30 show a third embodiment of the apparatus of the present invention, designated generally by the numeral 100 in FIG. 30. In FIGS. 18–27, there can be seen a mounting assembly that includes a mounting plate 99 and receptacle 112 (See FIGS. 20–21). An alternate receptacle 112A is shown in FIGS. 20A and 21A. The mounting plate 99 and receptacle 112 are positioned close to each other as shown in FIGS. 24–30 upon assembly. Mounting plate 99 has a central opening 101 and a periphery 102. The mounting plate 99 can be generally flat, providing opposed flat surfaces 103, 104. Receptacle 112 defines a mounting assembly with mounting plate 99 that can receive an insert such as members 27 and 28 that were described above with respect to the embodiment of FIGS. 1–12.

Insert 105 is similar to the insert of the embodiment of FIGS. 1–12, the difference being removal of tabs 32 (see FIG. 5). The embodiment of FIGS. 18–30 uses a receptacle 115 that is closely positioned to the plate 99 as shown in FIGS. 24–30. Insert 105 thus provides surfaces 21, 22, 23 as the insert shown in FIG. 5. The tabs 32 have been removed. The insert 105 has a smooth, flat undersurface 106. Curved surface 21 fits a cavity 119 of receptacle 115 during construction using the method of the present invention.

In FIGS. 19–21, receptacle 112 is comprised of a pair of flanges 113, 114 and an external curved wall 115. An opening 116 is provided in curved wall 115. The flanges 13, 14 provide arc shaped edges 117 and straight edge portions 118, 119. Arrows 120 in FIG. 22 illustrate the assembly of insert 105, mounting plate 99, and receptacle 112.

In FIGS. 20A and 21A, an alternate construction for the receptacle is shown as receptacle 124. Receptacle 124 has spaced apart semicircular walls 125, 126 that can be generally parallel to each other. External curved wall 127 spans between walls 125, 126. Opening 129 in receptacle 129 allows a wiring harness to pass therethrough. A cavity 128 is formed by walls 125, 126, 127. Each wall 125, 126 has a straight edge portion indicated as 130, 131 respectively in FIGS. 20A, 20B. Cavity 128 receives some electronic hearing aid components, similar to the cavity 122 of receptacle 112 (see FIGS. 29–30).

Figure 24:
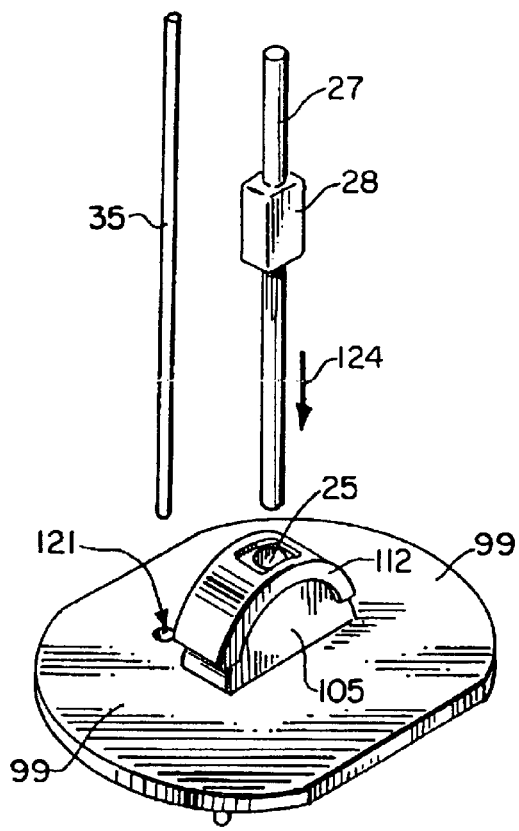
FIG. 24 is a fragmentary, perspective. exploded view of the third embodiment of the apparatus of the present invention illustrating the mounting member and insert portions thereof.
Figure 25:
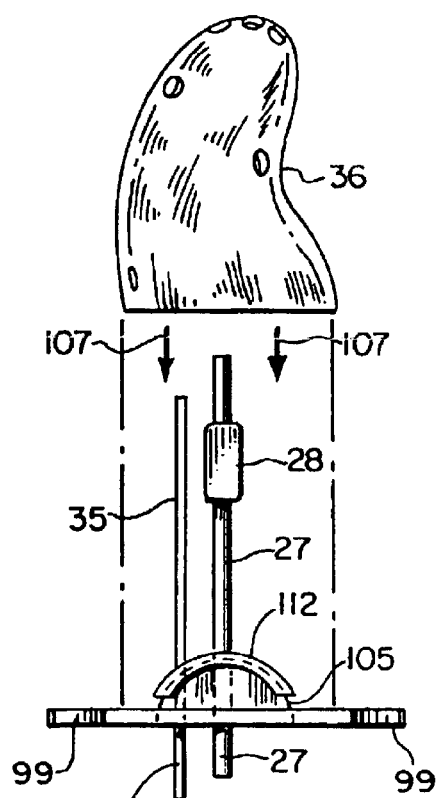
FIG. 25 is a side elevational view of the third embodiment of the apparatus of the present invention illustrating the method step of attaching the shell having a mold cavity to the mounting member and insert portions.
Figure 26:
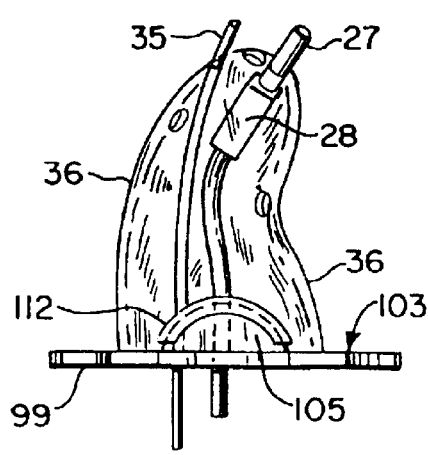
FIGS. 26 and 27 are perspective views illustrating method steps of the present invention including the filling of the mold cavity with elastomeric material to encapsulate the inserts and support the mounting members.
Figure 27:
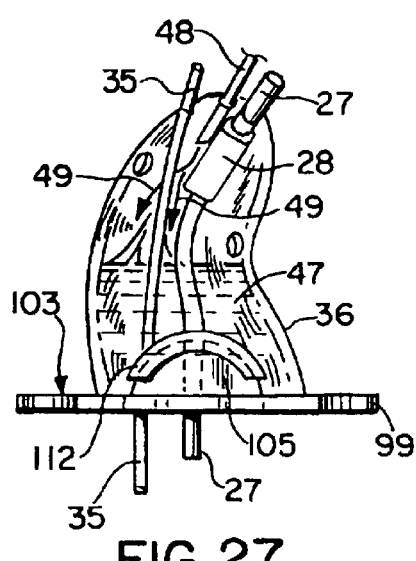

In FIG. 23, the insert 105, mounting plate 99, and receptacle plate 112 have been assembled in operating position before molding using shell 36. FIGS. 24–27 illustrate the molding steps of forming a soft polymeric body 108 about inserts 105, 35. Mounting plate 99 has an opening 121 that receives vent tube insert 35. Insert 105 has a cylindrically shaped open ended channel 25 that receives coated wire 27. Arrow 123 in FIG. 24 illustrates the assembly of coated wire insert 27 to cylindrically shaped opening 25 of insert 105. FIG. 25 shows the completed assembly of mounting plate 99, receptacle 112, insert 105, and insert 35. In FIG. 25, shell 35 is shown being lowered in the direction of arrows 107 until it fits over the inserts 105, 35, and registers against the flat surface 103 of mounting plate 99 as shown in FIGS. 26 and 27. As with the embodiment of FIGS. 1–12, the inserts 105, 35 extend through openings in the shell 36 so that when the inserts 35, 105 are removed after the soft polymeric body 108 is formed, they will leave behind recesses to be occupied by electronic hearing aid components.

In FIG. 27, needle 48 is shown injecting elastomeric material (eg. silicone) as indicated by the arrows 49 to the mold cavity formed inside of shell 36. After the elastomeric material 47 in FIG. 27 is allowed to set, shell 36 is removed as shown by arrows 124 in FIG. 28. A user then removes the inserts 35, 105 using thumb and forefinger 55, 56 as shown in FIG. 28. The arrow 54 in FIG. 28 indicates schematically the removal of the inserts to leave behind cavities 109, 110. In FIG. 29, a user or technician uses his or her thumb and finger 55, 56 to pull an electronic hearing aid package into the cavities 109, 110 in soft body 108. As with the embodiment of FIGS. 1–12, these components can include, for example battery door 58, battery 59, amplifier 60, microphone 61, wire harness 63, receiver 64, receiver sound tube 65, and vent tube 66.

In the embodiment of FIGS. 13–30, a technician can sever the wiring harness 84 after the electronic components that are contained within cavity 81 have been lifted upwardly to the position of FIG. 16, enabling those components to be serviced, replaced, etc. If the components below openings 95, 96 need to be serviced, those can be removed by either cutting the soft polymeric body 94 or by carefully removing them through expansion of the cavity in which they are contained.

PARTS LIST

The following is a list of suitable parts and materials for the various elements of the preferred embodiment of the present invention.

| | |
|---|---|
| 10 | hearing aid apparatus |
| 11 | modular face plate |
| 12 | surface |
| 13 | surface |
| 14 | stacking pin |
| 15 | central opening |
| 16 | periphery |
| 17 | vent tube opening |
| 18 | receptacle |
| 19 | insert |
| 20 | insert body |
| 21 | curved surface |
| 22 | flat surface |
| 23 | flat surface |
| 24 | flat surface |
| 25 | cylindrical bore |
| 26 | extraction handle |
| 27 | elongated coated wire |
| 28 | receiver replica insert |
| 29 | open ended bore |
| 30 | arrow |
| 31 | arrow |
| 32 | tab |
| 33 | socket |
| 34 | arrow |
| 35 | vent tube replica insert |
| 36 | mold |
| 37 | outer surface |
| 38 | wall |
| 39 | cavity |
| 40 | arrow |
| 41 | port |
| 42 | port |
| 43 | port |
| 44 | port |
| 45 | port |
| 46 | syringe |
| 47 | elastomer |
| 48 | needle |
| 49 | arrow |
| 50 | soft elastomeric body |
| 51 | outer surface |
| 52 | vent tube cavity |
| 53 | electronics cavity |
| 54 | arrow |
| 55 | technicians finger |
| 56 | technician's thumb |
| 57 | arrow |
| 58 | door |
| 59 | battery |
| 60 | amplifier |
| 61 | microphone |
| 62 | locking tabs |
| 63 | wire harness |
| 64 | receiver |
| 65 | receiver sound tube |
| 66 | vent tube |
| 67 | |
| 68 | |
| 69 | |
| 70 | hearing aid apparatus |
| 71 | mold |
| 72 | outer surface |
| 73 | wall |
| 74 | cavity |
| 75 | port |
| 76 | receptacle |
| 77 | curved wall |
| 78 | flat wall |
| 79 | flat wall |
| 80 | radially extending strut |
| 81 | cavity |
| 82 | receiver |
| 83 | receiver sound tube |
| 84 | wire harness |
| 85 | arrow |
| 86 | vent tube |
| 87 | arrow |
| 88 | arrow |
| 89 | door |
| 90 | battery |
| 91 | amplifier |
| 92 | microphone |
| 93 | locking tabs |
| 94 | soft polymeric body |
| 95 | opening |
| 96 | opening |
| 97 | socket |
| 98 | flat peripheral surface |
| 99 | mounting plate |
| 100 | hearing aid apparatus |
| 101 | opening |
| 102 | periphery |
| 103 | surface |
| 104 | surface |
| 105 | insert |
| 106 | surface |
| 107 | arrow |
| 108 | soft elastomeric body |
| 109 | vent tube cavity |
| 110 | electronics cavity |
| 111 | trimmed periphery |
| 112 | receptacle |
| 113 | flange |
| 114 | flange |
| 115 | external wall |
| 116 | opening |
| 117 | arc shaped edge |
| 118 | straight edge |
| 119 | straight edge |
| 120 | arrows |

-continued

| 122 | cavity |
| --- | --- |
| 123 | arrow |
| 124 | receptacle |
| 125 | semicircular wall |
| 126 | semicircular wall |
| 127 | external wall |
| 128 | cavity |
| 129 | opening |
| 130 | straight edge |
| 131 | straight edge |

The foregoing embodiments are presented by way of example only; the scope of the present invention is to be limited only by the following claims.

What is claimed is:

1. A method of manufacturing a hearing aid comprising the steps of:
   a) forming a hollow shell with a surface that approximates the shape of a patient's ear canal;
   b) providing a mounting member;
   c) mounting an electronic hearing aid component insert to the mounting member that simulates the shape of one or more electronic hearing aid components;
   d) placing the mounting member and insert in the hollow shell;
   e) filling the shell with a soft polymeric material that substantially encapsulates the insert;
   f) replacing the insert with one or more electronic hearing aid components; and
   g) wherein in step "e" the combination of insert and fill material define a soft structure that is compliant to ear canal movement during use.

2. The method of claim 1 further comprising the step of eliminating substantially all void space between the shell and the insert with the filling in step "f".

3. The method of claim 1 wherein step "c" comprises providing a mounting member includes a receptacle for holding an electronic hearing aid component.

4. The method of claim 1 wherein step "c" comprises providing a mounting member that is an acrylic member.

5. The method of claim 1 wherein in step "c" the mounting member has medial and lateral side portions.

6. The method of claim 5 wherein in step "d" some electronic hearing aid components are attached to the medial side portion of the mounting member.

7. The method of claim 1 wherein in steps "e", "f" and "g", filling includes encapsulating at least a receiver shaped electronic hearing aid component insert.

8. The method of claim 1 wherein steps "e", "f" and "g" comprise filling the shell with a soft silicone material that substantially encapsulates at least one of the electronic component inserts.

9. The method of claim 1 wherein the mounting member is a receptacle with a cavity and further comprising the step of placing a battery in the cavity.

10. The method of claim 9 wherein the mounting member includes a plate member and a separate receptacle member and further comprising the step of positioning the plate member and receptacle member next to each other.

11. The method of claim 1 further comprising the step of removing the insert and replacing the insert with a plurality of electronic hearing aid components.

12. The method of claim 1, wherein the hearing aid is sized to fit completely in the ear canal of a user.

13. A method of manufacturing a hearing aid comprising the steps of:
   a) forming a hollow shell with an inside surface that defines a mold cavity that approximates the shape of the human ear canal;
   b) providing an electronic hearing aid component insert;
   c) placing the insert within the mold cavity;
   d) filling the mold cavity with a soft polymeric material that substantially encapsulates the electronic component insert;
   e) allowing the soft polymeric fill material to cure;
   f) removing the insert to define a void space;
   g) placing one or more electronic hearing aid components in the void space, wherein in steps "e" and "f" the combination of the electronic components and fill material define a soft structure that is compliant to ear canal movement during use.

14. The method of claim 13 further comprising the steps of making an impression of the user's ear canal to construct a form and using the form in step "a" to shape the inside surface of the hollow shell.

15. The method of claim 13 further comprising the step of using a form to shape the mold cavity.

16. The method of claim 13 wherein the shell and mounting members are temporarily joined prior to step "d".

17. The method of claim 13 wherein in step "d" at least a receiver shaped insert is encapsulated.

18. The method of claim 13 wherein in step "d" at least a battery compartment insert and a receiver shaped insert are encapsulated.

19. The method of claim 13 wherein the mounting member is a battery compartment shaped insert.

20. The method of claim 13 wherein in step "b" the mounting member is of a hard plastic construction.

21. The method of claim 20 wherein the bonding layer includes multiple coatings applied to the mounting member.

22. The method of claim 13 wherein in step "b" the mounting member is a hard plastic and in step "e" the soft polymeric material includes silicone.

23. The method of claim 13, wherein the hearing aid is sized to fit completely in the ear canal of a user.

24. A method of manufacturing a hearing aid comprising the steps of:
   a) making a mold with a mold cavity that includes an inside surface that closely approximates the shape of a patient's ear canal;
   b) providing an insert that includes members having the size and shape of a number of selected electronic hearing aid components;
   c) placing the insert in the mold cavity;
   d) filling the mold cavity with a liquid polymeric material that substantially encapsulates at a portion of the insert;
   e) allowing the polymeric material to set;
   f) removing the insert to provide an insert cavity;
   g) replacing the insert with a hearing aid electronics package that fits the insert cavity;
   h) wherein the combination of polymeric material and electronics package define a soft hearing aid structure that is compliant to ear canal movement during use.

25. The method of claim 24, wherein the hearing aid is sized to fit completely in the ear canal of a user.

* * * * *